US012727863B2

(12) United States Patent
Hakim et al.

(10) Patent No.: US 12,727,863 B2
(45) Date of Patent: Sep. 8, 2026

(54) DETECTING LOW EJECTION FRACTION FROM ELECTROCARDIOGRAM DATA USING ARTIFICIAL INTELLIGENCE

(71) Applicant: Tempus AI, Inc., Chicago, IL (US)

(72) Inventors: Nicole Jane Rebecca Hakim, Miami, FL (US); Greg Sungyul Lee, Chicago, IL (US); Riccardo Miotto, New York, NY (US); RuiJun Chen, Livingston, NJ (US); John Michael Pfeifer, Lewisburg, PA (US); David Michael Vidmar, Florence, MA (US); Arun Nemani, Potomac, MD (US)

(73) Assignee: Tempus AI, Inc., Chicago, IL (US)

(*) Notice: Subject to any disclaimer, the term of this patent is extended or adjusted under 35 U.S.C. 154(b) by 0 days.

(21) Appl. No.: 18/821,307

(22) Filed: Aug. 30, 2024

(65) Prior Publication Data

US 2026/0060658 A1 Mar. 5, 2026

(51) Int. Cl.
*A61B 8/00* (2006.01)
*A61B 8/06* (2006.01)
*G16H 50/30* (2018.01)

(52) U.S. Cl.
CPC ............ *A61B 8/5284* (2013.01); *A61B 8/065* (2013.01); *A61B 8/5223* (2013.01); *G16H 50/30* (2018.01)

(58) Field of Classification Search
CPC ..... A61B 8/5284; A61B 8/065; A61B 8/5223; G16H 50/30
See application file for complete search history.

(56) References Cited

U.S. PATENT DOCUMENTS

2020/0397313 A1* 12/2020 Attia ...................... A61B 5/318
2021/0259560 A1* 8/2021 Venkatraman ......... A61B 5/024
2021/0361217 A1* 11/2021 Attia ...................... G16H 50/30
2022/0378379 A1 12/2022 Zimmerman
2023/0397888 A1 12/2023 Golan et al.
(Continued)

FOREIGN PATENT DOCUMENTS

EP 4417127 A1 8/2024
WO 2023214647 A1 11/2023
WO 2024112915 A2 5/2024

OTHER PUBLICATIONS

International Search Report and Written Opinion, dated Mar. 19, 2025, for Internation Patent Application No. PCT/US2024/044828. (15 pages).

*Primary Examiner* — Bo Joseph Peng
(74) *Attorney, Agent, or Firm* — Seed Intellectual Property Law Group LLP

(57) ABSTRACT

Techniques for detecting low ejection fraction (EF) from electrocardiogram (ECG) data using artificial intelligence (AI) are disclosed. ECG data is obtained for a patient. The ECG data is provided as input to a plurality of trained AI models, wherein each trained AI model is trained to determine a score of low EF based on the ECG data. A score of low EF is determined using each trained AI model based on the ECG data. An overall score of low EF is determined based on a combination of the scores of low EF determined by each of the trained AI models. An operating point threshold is obtained for the patient based on a plurality of patient characteristics. The overall score of low EF is compared to the operating point threshold. A low EF prediction is made for the patient based on the comparison.

19 Claims, 8 Drawing Sheets

(56) References Cited

U.S. PATENT DOCUMENTS

| | | | | |
|---|---|---|---|---|
| 2024/0206821 | A1* | 6/2024 | Upadhyay | A61B 5/318 |
| 2024/0341660 | A1* | 10/2024 | Attia | A61B 5/347 |
| 2024/0378437 | A1* | 11/2024 | Friedman | G06N 3/084 |

* cited by examiner

DETECTING LOW EJECTION FRACTION FROM ELECTROCARDIOGRAM DATA USING ARTIFICIAL INTELLIGENCE

BACKGROUND

Ejection fraction (EF) is a measurement of a percentage of total blood in a person's heart that is pumped with each heartbeat. Low ejection fraction is correlated with serious cardiovascular conditions such as clinical heart failure. Detecting low ejection fraction allows patients to receive treatment for the condition, improving patient outcomes.

BRIEF SUMMARY

Techniques for detecting low ejection fraction (EF) from electrocardiogram (ECG) data using artificial intelligence (AI) are disclosed. ECG data is obtained for a patient. The ECG data is provided as input to a plurality of trained AI models, wherein each trained AI model is trained to determine a score of low EF based on the ECG data. A score of low EF is determined using each trained AI model based on the ECG data. An overall score of low EF is determined based on a combination of the scores of low EF determined by each of the trained AI models. An operating point threshold is obtained for the patient based on a plurality of patient characteristics. The overall score of low EF is compared to the operating point threshold. A low EF prediction is made for the patient based on the comparison.

DETAILED DESCRIPTION

Figure 1:
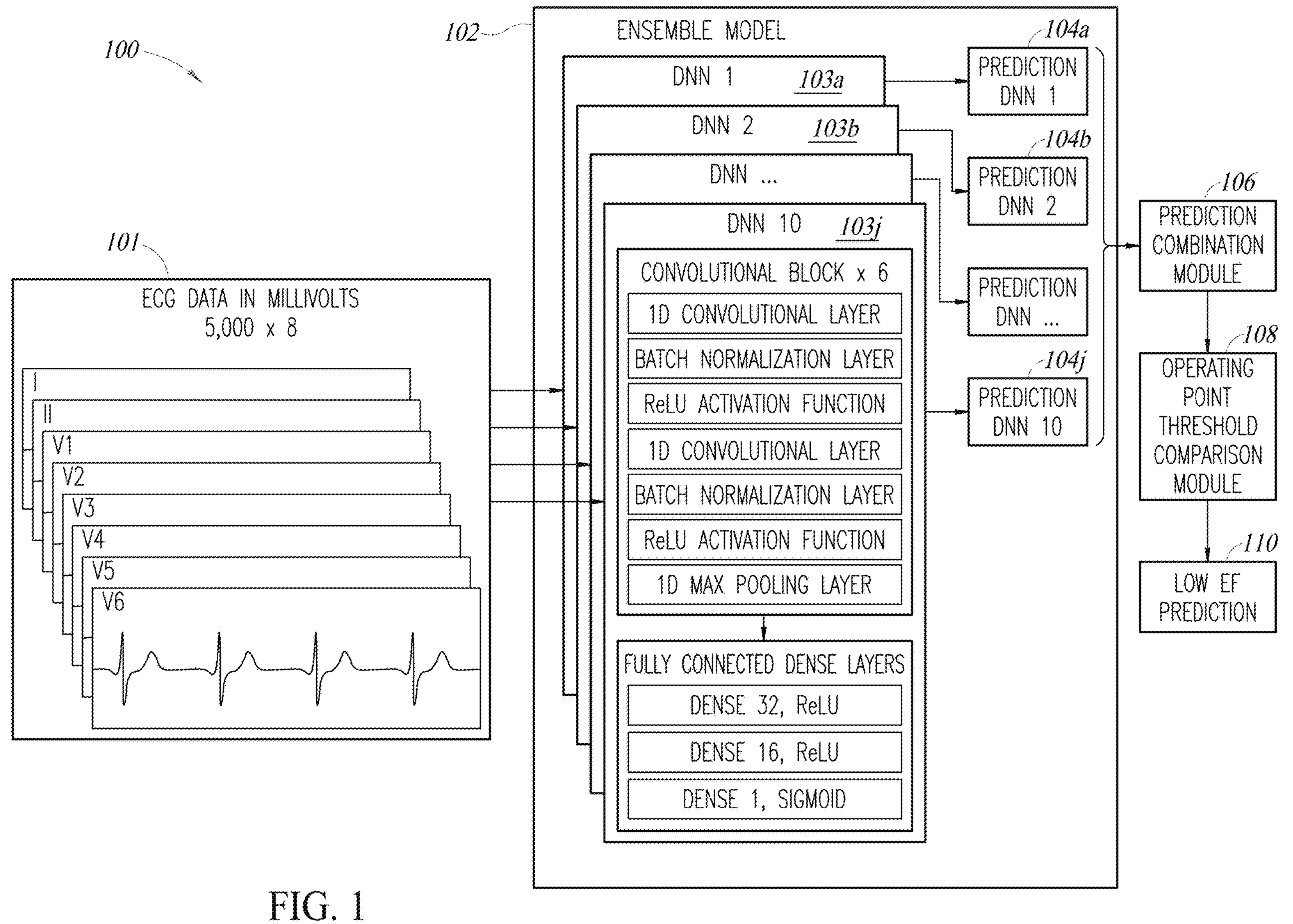
FIG. 1 is a diagram illustrating data flow in a system used to detect low ejection fraction from electrocardiogram data according to some embodiments.

Cardiovascular disease (CVD) is the leading cause of mortality in the United States and worldwide. Ejection fraction (EF) refers to a percentage of total blood pumped out of the heart with each heartbeat. EF values between 55% and 75% typically indicate normal heart function. But low EF, such as 40% or lower, is a sign that the heart isn't pumping enough blood, and that the patient may have a cardiovascular disease. Patients with low EF are at increased risk of developing clinical heart failure, which often leads to serious health complications or death.

Low EF is typically diagnosed using a transthoracic echocardiogram (i.e., "echo" or "TTE"), which is a procedure for assessing cardiovascular function based on ultrasound images of cardiovascular features. Because echos tend to be expensive and require specialized training to administer, they are often only performed on patients who care providers have reason to believe may have impaired cardiovascular function. Most patients, therefore, do not have echo data on file until after they have shown symptoms of cardiovascular disease. This creates a significant care gap, wherein care providers do not have sufficient information to provide preventative care or early interventional care for conditions associated with low EF. Medications exist that can improve low EF and decrease patients' risk of developing clinical heart failure. Therefore, detection of undiagnosed low EF may enable treatment that has direct, positive impacts on the lives of patients, and may reduce the likelihood of cardiovascular disease and death.

In response to these disadvantages in conventional patient care, the inventors have conceived of techniques for detecting low ejection fraction from electrocardiogram data using artificial intelligence. Unlike echos, electrocardiogram measurements (i.e. "ECGs") are part of routine patient care and are present in most patients' records. Thus, ECGs can be used to determine EF for many patients for whom echo data is unavailable. Additionally, techniques disclosed herein enable ECGs to be used to identify subjects who may have an underlying cardiovascular condition diagnosable using an echo.

Artificial intelligence models are used to enable improved detection and diagnosis of low ejection fraction. In particular, an ensemble model is trained on 12-lead electrocardiogram (ECG) data to predict whether a patient has low EF. Ensemble models aggregate predictions from multiple models and typically outperform single models because they aggregate the strengths of multiple algorithms, reduce the likelihood of overfitting, and balance out individual errors, leading to more accurate and robust predictions. Multiple operating points are used to categorize (e.g., binarize) the ensemble model's continuous output. Using multiple operating points provides the ability to tailor the model's behavior for different sub-populations of patients, better ensuring that the model's performance is consistent across groups. Thus, data collected during standard of care may be leveraged to provide more robust, accurate, and equitable detection of undiagnosed cardiovascular disease.

In some embodiments electrocardiogram (ECG) data is obtained for a patient. The ECG data is provided as input to an ensemble of trained artificial intelligence (AI) models, wherein each trained AI model is trained to determine a score of low ejection fraction (EF) based on the ECG data. A score of low EF is determined using each trained AI model based on the ECG data. An overall score of low EF is determined based on a combination of the scores of low EF determined by each of the trained AI models. An operating point threshold is obtained for the patient based on characteristics of the patient such as their sex assigned at birth and their age. The overall score of low EF is compared to the operating point threshold. An indication of low EF is determined for the patient based on the comparison.

In some embodiments, the operating point threshold is obtained to minimize a difference between sensitivity and specificity of binary low EF predictions made using the trained AI models for patients having the patient characteristics.

In some embodiments, the operating point threshold is based on an indication of sex of the patient, an indication of age of the patient, or a combination thereof.

In various embodiments, two or more trained AI models of the ensemble of trained AI models have a same architecture.

As used herein, the phrase "training data" may refer to one or more of a training dataset, a tuning dataset, an operating point dataset, or any combination thereof.

FIG. 1 is a diagram illustrating data flow in a system 100 used to detect low ejection fraction from electrocardiogram data according to some embodiments.

System 100 includes ECG data 101, ensemble model 102, prediction combination module 106, operating point threshold comparison 108, and low EF prediction 110.

ECG data 101 includes data from 12-lead ECG test. 12-lead ECG tests typically produce 12 sets of timeseries data corresponding to each of 12 leads contacting a patient during the test. During a 12-lead ECG test, leads V1, V2, V3, V4, V5, and V6 contact the patient's chest, while leads I, II, III, IV, V, and VI contact the patient's limbs.

As shown in FIG. 1, ECG data 101 includes timeseries data corresponding to limb leads I and II, and chest leads V1, V2, V3, V4, V5, and V6. But the disclosure is not so limited. In various embodiments, any combination of timeseries data corresponding to chest leads, limb leads, or any combination thereof, is used. Additionally, data obtained using any non-standard configuration of ECG leads may be used. In some embodiments, the non-standard configuration of ECG leads includes using fewer leads, such as by using an accessory as described in U.S. application Ser. No. 17/814,229, which is hereby incorporated by reference in its entirety. While FIG. 1 indicates that 5,000 datapoints are included for each timeseries, the number of datapoints in ECG data 101 may vary based on a sample rate of the ECG machine used to measure the ECG data or other factors.

Ensemble model 102 includes one or more artificial intelligence (AI) models such as trained AI model 103*a*, 103*b*, or 103*j* (collectively, "trained AI models 103" or "AI models 103"), which are trained to determine a score of low ejection fraction (EF) based on ECG data 101. In various embodiments, each of the one or more trained AI models receives each timeseries data of ECG data 101. In some embodiments, each of the one or more trained AI models is provided with a portion of the timeseries data of ECG data 101. For example, a first trained AI model may be provided with timeseries data associated with a first set of limb leads, chest leads, or any combination thereof. A second trained AI model may be provided with timeseries data associated with a second set of limb leads, chest leads, or any combination thereof. In some embodiments, each trained AI model is provided with a same set of timeseries data.

Each trained AI model in trained AI models 103 is trained to determine a score of low EF based on ECG data 101. As depicted in FIG. 1, trained AI models 103 are convolutional neural networks ("CNNs") including 6 convolutional blocks and output layers comprising 3 fully connected dense layers. In various embodiments, any artificial intelligence model suitable for processing timeseries data is used. For example, trained AI models 103 may include one or more long short-term memory networks ("LSTMs"), recurrent neural networks ("RNNs"), gated recurrent units ("GRUs"), transformers, etc.

While AI model 103*j* is illustrated as including six convolutional blocks and three fully connected dense layers, the disclosure is not so limited. In various embodiments wherein an AI model of AI models 103 includes a convolutional neural network, any combination of one or more convolutional blocks and one or more output layers is used. Moreover, the convolutional blocks may include any number of convolutional layers, batch normalization layers, and activation functions in any configuration.

In some embodiments, each AI model of AI models 103 has a same architecture. In some embodiments, at least two AI models of AI models 103 have different architectures. In some embodiments, each AI model of AI models 103 is initialized using a same seed. In some embodiments, at least two AI models of AI models 103 are initialized using different seeds.

AI models 103 are not necessarily configured to directly process time series data of ECG data 101. In some embodiments, signal processing is used to extract features of ECG data 101. For example, signal processing techniques such as principal component analysis (i.e., "PCA"), Fast Fourier Transform (i.e., "FFT"), wavelet transform, etc. may be used to extract features of ECG data 101 to be processed by one or more AI models in AI models 103. Accordingly, an AI model of AI models 103 may be configured to take as input a feature computed by applying signal processing to ECG data 101 instead of, or in addition to, ECG data 101 itself.

In some embodiments wherein signal processing is used to extract features from ECG data 101, AI models 103 include any kind of AI model suitable for predicting a score of low EF based on the extracted features such as one or more support vector machines (i.e., "SVMs"), decision trees, linear regression models, logistic regression models, feed-forward neural networks, etc., or any combination thereof.

In various embodiments, AI models 103 includes any combination of AI models configured to process time series data of ECG data 101 or AI models configured to process features of ECG data 101 obtained using signal processing techniques.

AI models 103 produce prediction 104*a*, prediction 104*b*, and prediction 104*j* (collectively, "predictions 104") based on ECG data 101. In various embodiments, predictions 104 represent scores that ECG data 101 is from a patient that has low ejection fraction as determined by each of the AI models.

Prediction combination module 106 is configured to combine predictions 104 into an overall prediction of low EF. In some embodiments, prediction combination module 106 calculates an average of predictions 104 such as a mean, median, or mode. In some embodiments, prediction combination module 106 computes a weighted combination of predictions 104. In some such embodiments, the weights for calculating the weighted combination are learned, such as by freezing weights of ensemble model 102 and learning the weights by comparing the weighted combination of outputs produced using AI models 103 to a label indicating whether ECG data 101 indicates low EF.

Operating point threshold comparison module 108 is configured to compare the overall prediction to an operating point threshold to produce low EF prediction 110. The operating point threshold may be determined based on various characteristics of the ECG data such as a binarized age of the patient, a binarized sex of the patient, or both. In various embodiments, the characteristics of the ECG data are quantized in ways other than binarization, such as by binning values of the characteristics into any number of bins.

In some embodiments, the operating point threshold is determined based on user input, such as user input specifying the presence or absence of one or more low EF risk factors or conditions correlated with low EF. In one non-limiting example, the operating point threshold is based on user input characterizing a level of cardiovascular activity of the patient, such as on a scale from 1-10. In this example, user input indicating low cardiovascular activity lowers the operating point threshold such that a lower overall prediction is determined to indicate low EF. Determining the operating point threshold is discussed in detail with respect to FIG. 6.

Low EF prediction 110 indicates whether a patient associated with ECG data 101 is determined to have low EF. In some embodiments, low EF prediction 110 includes a binary classification, such as 0 or 1. For example, 0 may indicate that the patient does not have low EF, while 1 may indicate that the patient does have low EF. In some embodiments, low EF prediction 110 includes a multi-class classification. For example, the patient may be classified as very low risk, low risk, medium risk, high risk, or very high risk. In various embodiments, low EF prediction 110 classifies the patient into one or more of any number of classes.

Figure 2:
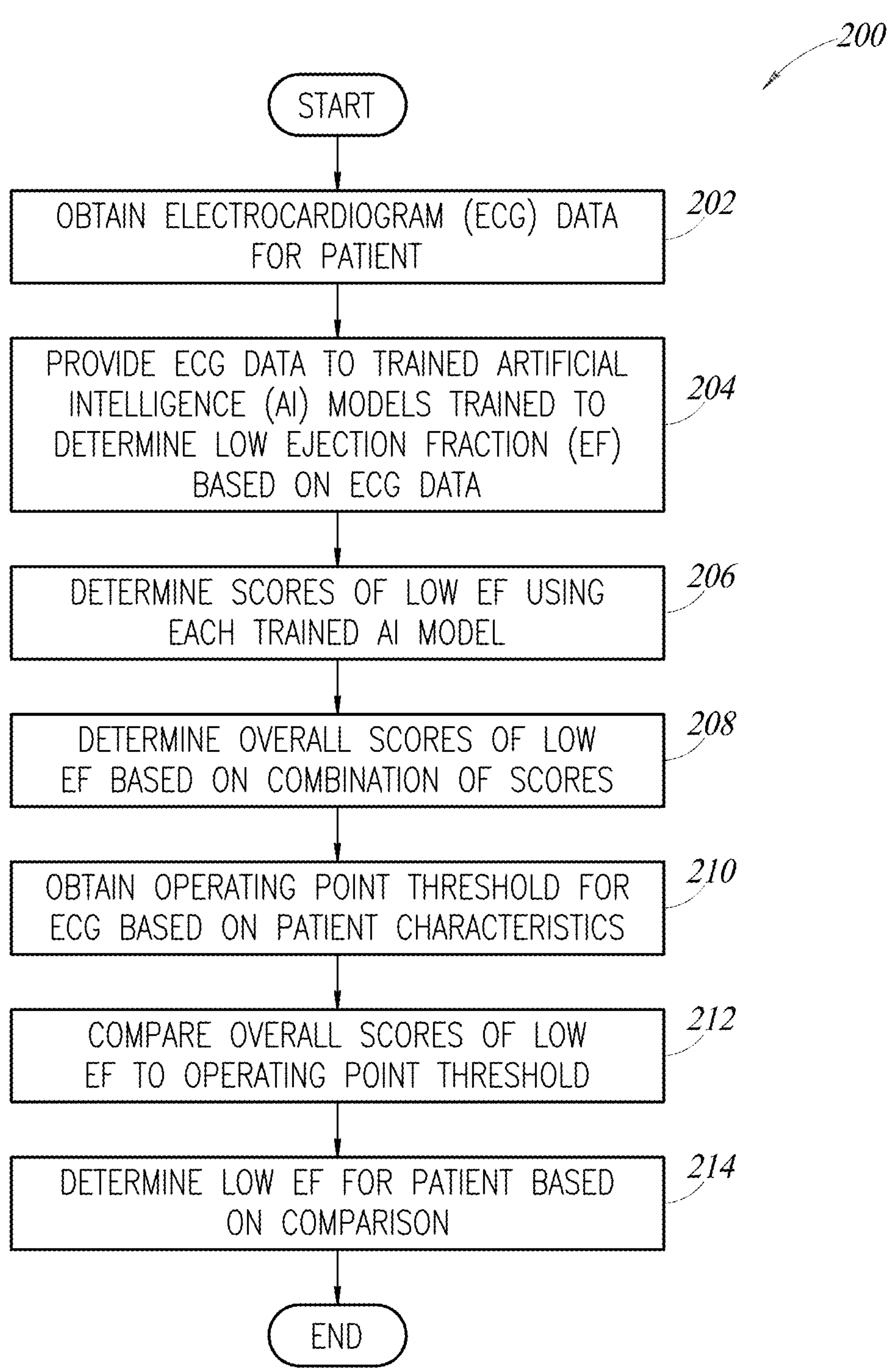
FIG. 2 is a logical flow diagram illustrating a process used to detect low ejection fraction from electrocardiogram data using artificial intelligence according to some embodiments.

FIG. 2 is a logical flow diagram illustrating a process 200 used to detect low ejection fraction from electrocardiogram data using artificial intelligence according to some embodiments. Process 200 begins, after a start block, at block 202, where electrocardiogram (ECG) data for a patient is obtained.

In some embodiments, the ECG data is obtained in real-time or near real-time from a patient, such as while an ECG measurement is being performed on the patient. In some embodiments, the ECG data is obtained from a database. After block 202, process 200 continues to block 204.

At block 204, the ECG data is provided to AI models trained to determine low EF based on the ECG data. As discussed herein, the ECG data may include data corresponding to timeseries data associated with any combination of leads of a 12 lead ECG test. In some embodiments, the ECG data includes 8-lead ECG data or any other kind of ECG data.

In some embodiments, various patient characteristics are also provided as input to one or more of the AI models. For example, an age or sex of the patient may also be provided as input to one or more of the AI models. After block 204, process 200 continues to block 206.

At block 206, likelihoods of low ejection fraction are determined using each trained AI model. In some embodiments, the trained AI models are configured to produce a continuous value such as a value between 0 and 1 that corresponds to a score indicating that the patient has low EF. After block 206, process 200 continues to block 208.

At block 208, an overall score of low ejection fraction is determined based on a combination of the scores of low ejection fraction.

In some embodiments, the scores produced using the trained AI models are mapped to the overall score of low ejection fraction using an average of the scores of low ejection fraction such as a mean, median, or mode.

In various embodiments, any mapping between the scores produced by each trained AI model and the overall score is used.

In some embodiments, the overall score of low EF is determined based on a maximum score of EF determined by an AI model. For example, when the scores are [0.42, 0.37, 0.63, 0.79], the overall score of low EF may be determined to be 0.79.

In some embodiments, the overall score of low ejection fraction is a weighted combination of the scores of low ejection fraction. For example, one or more weights may be associated with each score produced by a trained AI model. In some embodiments, the weights are determined based on the number of trained AI models in ensemble model 102. For example, when ensemble model 102 includes five trained AI models, each weight may be 0.2. In some embodiments, the weights are based on a type of each AI model in ensemble model 102. For example, a first type of AI model may be associated with a weight of 0.4, and a second type of AI model may be associated with a weight of 0.6. In some embodiments, the weights are based on a performance metric of the AI model, a size of the AI model such as number of weights associated with the AI model, etc.

In some embodiments, the weights comprise one or more output layers, which compute the overall low EF score based on the scores of low EF. In some embodiments, after each of the trained AI models are trained, weights associated with the one or more output layers are trained in a second training phase. In some such embodiments, weights associated with the trained AI models are frozen, and the output layers are trained based on comparison of the determination of low EF produced at block 214 to a corresponding label. Thus, the prediction combination module may be trained to combine the scores of low EF into the overall low EF score. After block 208, process 200 continues to block 210.

At block 210, an operating point threshold for the ECG is determined based on patient characteristics. In some embodiments, the operating point threshold is determined by retrieving the operating point threshold that corresponds to the patient characteristics. In some embodiments, the operating point threshold is selected to minimize a difference between a sensitivity and specificity of ensemble model 102 with respect to patients having the patient characteristics. Selection of operating point thresholds is described in detail with respect to FIG. 6, and examples of various operating point thresholds are shown in FIG. 7. After block 210, process 200 continues to block 212.

At block 212, the overall score of low ejection fraction is compared to the operating point threshold. After block 212, process 200 proceeds to block 214.

At block 214, a determination of whether the ECG indicates low ejection fraction is made based on the comparison. In some embodiments, the patient is determined to have low ejection fraction when the overall score of low ejection fraction is greater than the operating point threshold. After block 214, process 200 ends at an end block.

As discussed herein, process 200 may be performed in real-time or near real-time when an ECG measurement is being taken for the patient. The determination may be used to recommend performance of a transthoracic echocardiogram (i.e., "echo") while the patient is at a medical care facility, automatically schedule the patient for an echo, alert a care provider that the patient may have low ejection fraction, etc. Low EF determination in real-time or near real-time with respect to collection of the ECG data may enable care providers to more expeditiously and efficiently address the low EF because the patient is already at the care facility. This may improve patient outcomes by lowering the amount of time the low EF goes untreated.

In various embodiments, the operating point threshold is applied to each score of low ejection fraction before the scores are combined at block 208. Thus, each AI model may classify the ECG data as indicating low EF or not indicating low EF. In some such embodiments, the overall score of low EF is determined based on a number of AI models that classify the ECG data as indicating low EF. For example, when 7 AI models produce output greater than the operating point threshold and 3 AI models produce output less than the operating point threshold, the overall score may be determined to be 0.70.

Figure 3:
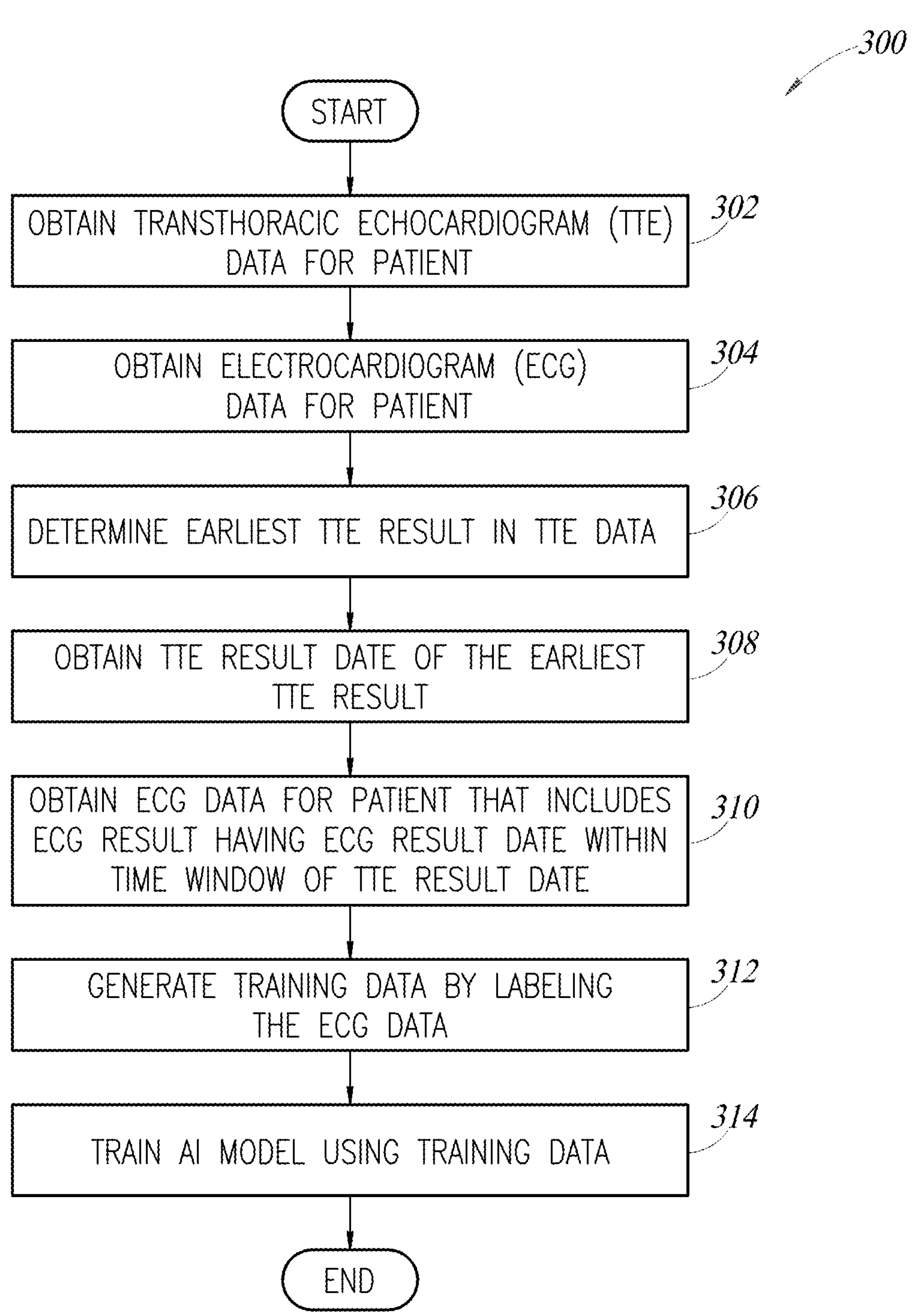
FIG. 3 is a logical flow diagram illustrating a process used to generate training data for training an artificial intelligence model to detect low ejection fraction from electrocardiogram data according to some embodiments.

FIG. 3 is a logical flow diagram illustrating a process 300 used to generate training data for training an artificial intelligence model to detect low ejection fraction from electrocardiogram data according to some embodiments. Process 300 generates training data based on an earliest available echo result for a patient.

Process 300 begins, after a start block, at block 302, where transthoracic echocardiogram (i.e., "TTE" or "echo") data for a patient is obtained. TTE data may be used to accurately determine whether a patient has low ejection fraction. Thus, the TTE data may be used as ground truth for creating the training data.

In some embodiments, the TTE data comprises one or more fields corresponding to one or more ejection fraction values. The TTE data may include a continuous value between 0 and 1 corresponding to the ejection fraction.

While TTE data may be used to determine whether a patient has low EF for purposes of creating training data, the disclosure is not so limited. In various embodiments, any measurement usable to diagnose low EF may be used as ground truth in creating the training data. For example, a diagnosis of low EF based on magnetic resonance imaging (i.e., "MRI") data may also be used as ground truth in constructing the training dataset. After block 302, process 300 continues to block 304.

At block 304, electrocardiogram (i.e., "ECG") data for the patient is obtained. After block 304, process 300 continues to block 306.

At block 306, an earliest TTE result in the TTE data is determined. For example, several TTE results may be available for the patient. In some embodiments, whether the patient has low EF may therefore be determined based on the first TTE result in time. For example, if the patient's first TTE result indicates that the patient has low EF, one or more ECGs associated with the patient may be labeled as indicative of low EF.

In some embodiments, the TTE data is determined to indicate low EF when the TTE data satisfies a threshold ejection fraction. For example, when the threshold ejection value is 40%, ejection fractions above 40% are determined to not indicate low EF, while ejection fractions equal to or under 40% are determined to indicate low EF. While the threshold ejection fraction is typically between 35% and 55%, in various embodiments, the threshold ejection fraction is any ejection fraction less than 70%. After block 306, process 300 continues to block 308.

At block 308, a TTE result date of the earliest TTE result is obtained. After block 308, process 300 continues to block 310.

At block 310, ECG data for a patient that includes ECG results having an ECG result date within a time window of the TTE result date is obtained.

In some embodiments, the time window comprises 1-8 weeks before the TTE result date. In some embodiments, the time window comprises 1-8 weeks after the TTE result date. By including ECG data that is close in time to the TTE result date, ECG data that may be inconsistent with the TTE data may be excluded. For example, if a patient has recently developed low EF as indicated by TTE results, ECG results from several years ago may not reflect the low EF.

In some embodiments, the ECG data only includes an ECG result having a date closest to the TTE result date in the time window. Thus, the ECG data may be more likely to capture time-sensitive information associated with the TTE results. After block 310, process 300 continues to block 312.

At block 312, training data is generated by labeling the ECG data. In some embodiments, the ECG data is labeled based on the determination of whether the earliest TTE result indicates low EF made at block 306. For example, the ECG data may be labeled with a "1" if the ECG data is associated with low EF, or a "0" if the ECG data is not associated with low EF. After block 312, process 300 continues to block 314.

At block 314, an AI model is trained using the training data. The AI model is provided with the ECG data as input. Based on the ECG data, the AI model determines a score indicating whether the patient associated with the ECG data has low EF. The score is then compared to the label associated with the ECG data, and the AI model is trained based on the comparison. After block 314, process 300 ends at an end block.

While for ease of discussion process 300 is described in terms of training one AI model with one example of labeled ECG data, process 300 is typically performed many times to create datasets including hundreds or thousands of samples of labeled ECG data. Furthermore, embodiments of process 300 may be used to train any number of AI models, such as 10 or more models to be used in an ensemble.

Figure 4:
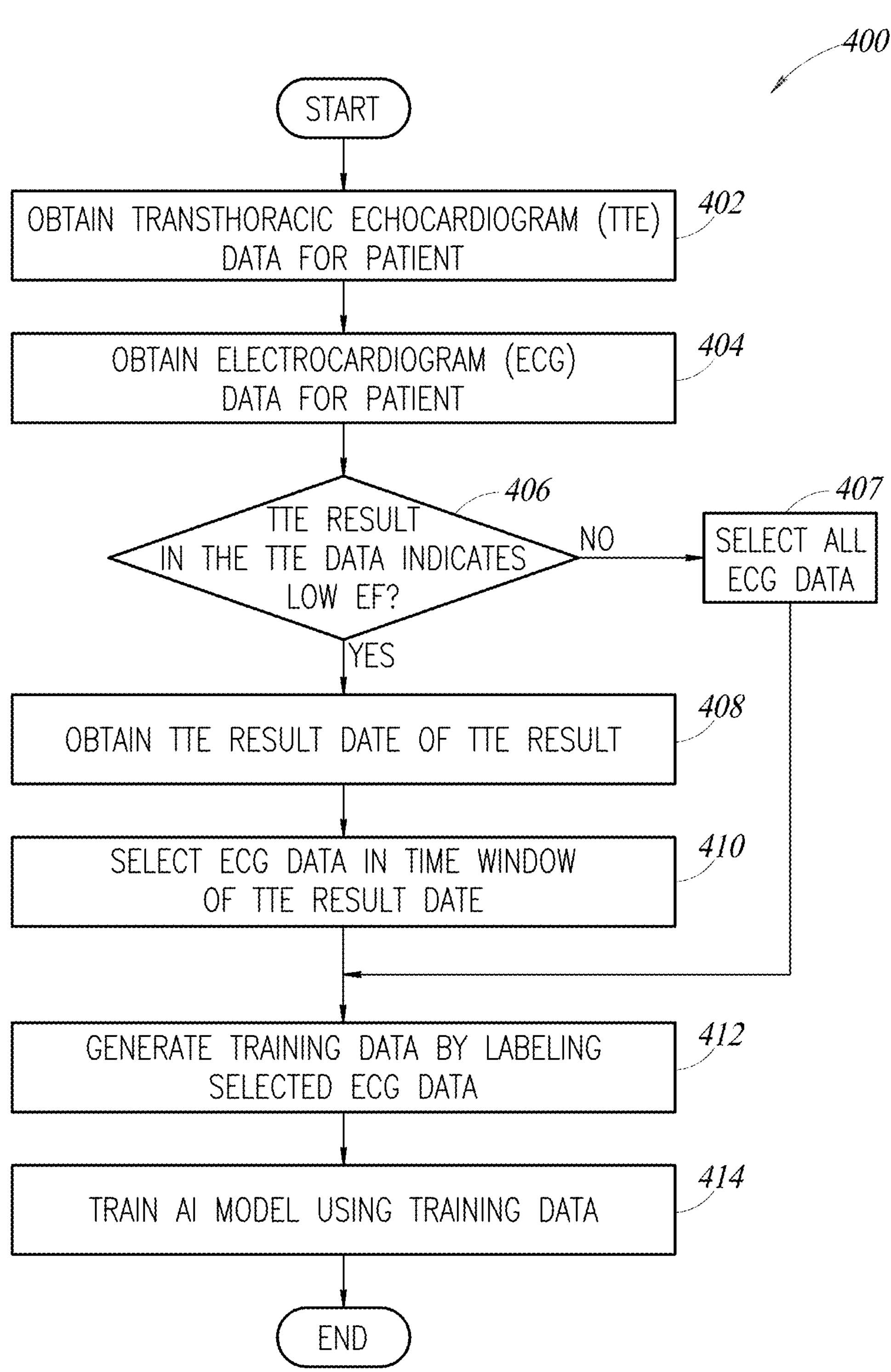
FIG. 4 is a logical flow diagram illustrating a process used to generate training data for training an artificial intelligence model to detect low ejection fraction from electrocardiogram data according to some embodiments.

FIG. 4 is a logical flow diagram illustrating a process 400 used to generate training data according to some embodiments. In contrast to process 300, which generates training data based on an earliest available transthoracic echocardiogram result, process 400 generates training data based on whether any available transthoracic echocardiogram result for a patient indicates low EF.

Process 400 begins, after a start block, at block 402, where transthoracic echocardiogram (i.e., "TTE" or "echo") data for a patient is obtained. After block 402, process 400 continues to block 404.

At block 404, electrocardiogram (i.e., "ECG") data for the patient is obtained. After block 404, process 400 continues to block 406.

At block 406, a determination whether any TTE result in the TTE data indicates low EF is made. If no, process 400 continues to block 407. If yes, process 400 continues to block 408.

At block 407, all ECG data for the patient is selected. Because none of the TTE results associated with the patient indicate low EF, each of the patient's ECG results may be used as samples that do not indicate low EF.

At block 408, a TTE result date of a positive TTE result is obtained. Because at least one TTE result of the patient indicates low EF, ECG data for the patient may be used as samples that indicate low EF. After block 408, process 400 continues to block 410.

At block 410, ECG data in a time window of the TTE result date is selected. In some embodiments, the time window comprises 1-8 before the TTE result date. In some embodiments, the time window comprises 1-12 weeks after the TTE result date. In some embodiments, the time window comprises 1-12 weeks before and 1-12 weeks after the TTE result date. In some embodiments, the time window includes all dates after the TTE result date and before a future negative echo for the patient or the patient's most recent encounter. After block 410, process 400 continues to block 412.

At block 412, training data is generated by labeling the selected ECG data. In various embodiments, block 412 employs embodiments of block 312 to label the selected ECG data. After block 412, process 400 proceeds to block 414.

At block 414, an AI model is trained using the training data. In various embodiments, block 414 employs embodiments of block 414 to train the AI model using the training data. After block 414, process 400 ends at an end block.

While for ease of discussion process 400 is described in terms of training one AI model with one example of labeled ECG data, process 400 is typically performed many times to create datasets including hundreds or thousands of samples of labeled ECG data. Furthermore, embodiments of process 400 may be used to train any number of AI models, such as 10 or more models to be used in an ensemble.

Figure 5:
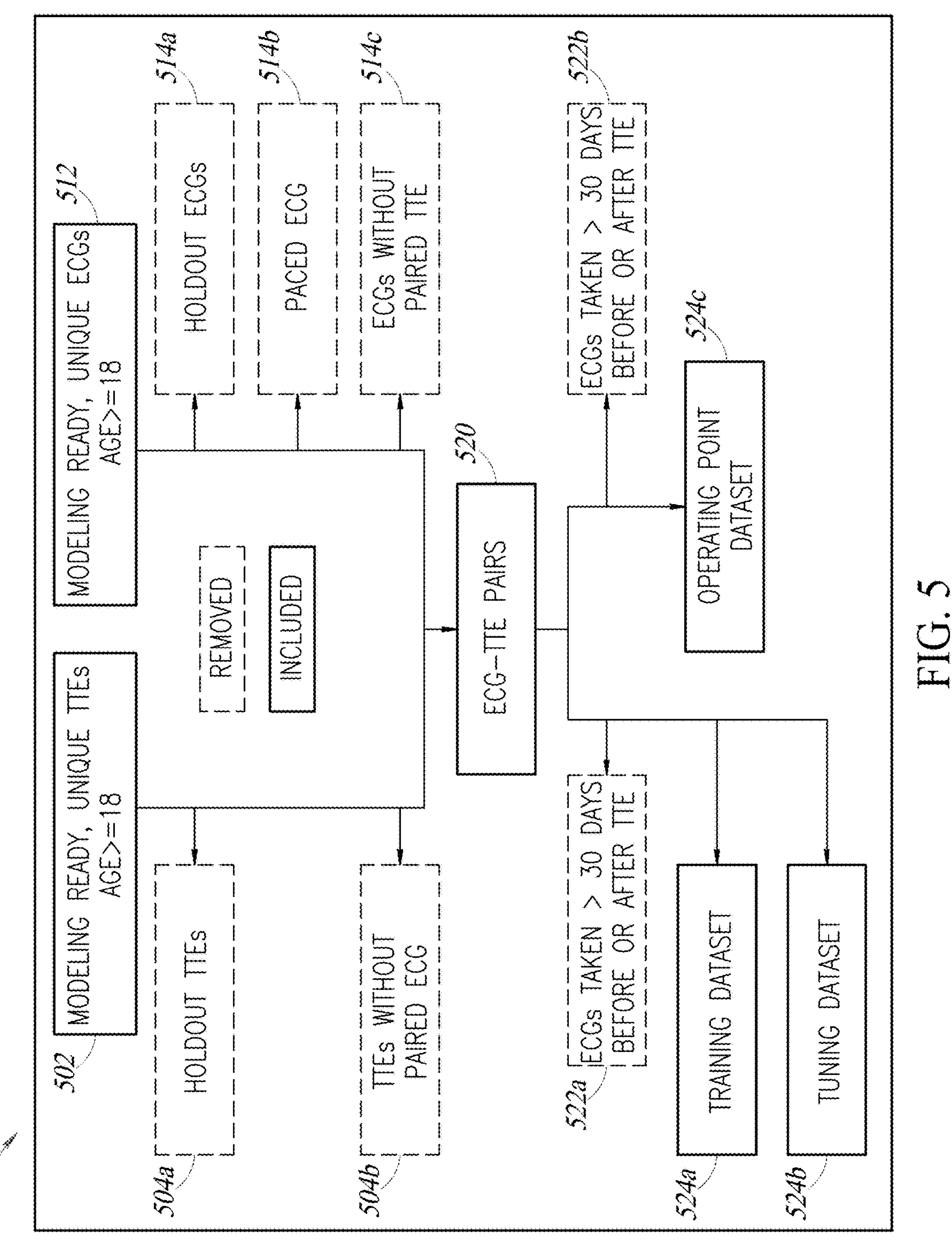
FIG. 5 is a diagram illustrating a process used to generate training data for training an artificial intelligence model to detect low ejection fraction from electrocardiogram data according to some embodiments.

FIG. 5 is a diagram illustrating a process 500 used to generate training data including one or more of a training dataset, a tuning dataset, or an operating point datasets according to some embodiments. As illustrated in FIG. 5, elements with dashed boxes are removed from the training data to create training dataset 524*a*, tuning dataset 524*b*, or operating point dataset 524*c*.

To create the various datasets, subsets of paired ECG and TTE data are created. Starting with unique TTE data for patients ages 18 and up 502, holdout TTEs 504*a* and TTEs without corresponding ECGs 504*b* are removed. Starting with unique ECG data for patients ages 18 and up 512, holdout ECGs 514*a*, paced ECGs 514*b*, and ECGs without corresponding TTEs 514*c* are removed. ECG-TTE pairs 520 represents pairs of corresponding ECG and TTE data for patients.

Training dataset 524*a* may be used to train AI models to detect low ejection fraction from electrocardiogram data as discussed herein. Tuning dataset 524*b* may be used to validate AI models trained to detect indications of low ejection fraction from electrocardiogram data.

Operating point data set 524*c* may be used to determine operating points for patients having certain patient characteristics. As described herein, ensemble model 102 may perform differently on different populations of patients. For example, at a given threshold, ensemble model 102 may have lower sensitivity but higher specificity in certain populations of patients such as younger women, whereas ensemble model 102 may have higher sensitivity but lower specificity in certain other populations of patients such as older men. To ensure that ensemble model 102 performs adequately across various relevant populations of patients, separate threshold operating points may be determined for each relevant population based on performance of ensemble model 102 on operating point dataset 524*c*. An example process for determining an operating point based on an operating point data set is discussed with respect to FIG. 6, and various example operating points are described with respect to FIG. 7.

Paced ECGs 514*b* refers to ECG data taken from patients who have pacemakers that are actively operating while the ECG data is being taken. The relationship between ECG data and low EF may vary in patients who have actively operating pacemakers. Therefore, in some embodiments, paced ECG data is omitted from training data set 524*a*, tuning data set 524*b*, or operating point data set 524*c*. In some embodiments, one or more of training data set 524*a*, tuning data set 524*b*, or operating point data set 524*c* include paced ECGs 514*b*. In some embodiments, ensemble model 102 is trained to detect whether ECG data is taken from a patient with an actively operating pacemaker.

To produce training dataset 524*a* and tuning dataset 524*b*, ECGs taken more than 30 days before or after corresponding ECGs 522*a* may be removed. To produce operating point dataset 524*c*, ECGs taken more than 30 days before or after corresponding ECGs 522*b* may be removed.

In some embodiments, operating point data set 524C includes ECGs having a prevalence of low EF samples between 5% and 15%. In some embodiments, operating point data set 524*c* includes ECGs with an ECG-level prevalence of low EF samples that matches that of training dataset 524*a*. In some embodiments, operating point dataset 504C includes ECGs having an ECG-level prevalence of low EF samples that matches that of tuning dataset 524*b*.

In some embodiments, datasets 524 include multiple ECGs per patient. In some embodiments, datasets 524 include one ECG per patient.

In various embodiments, training dataset 524*a*, tuning dataset 524*b*, or operating point dataset 524*c* are generated to include ECGs taken more than 30 days before or after the TTE 522*a* or 522*b*.

In some embodiments, training dataset 524*a*, tuning dataset 524*b*, or operating point dataset 524*c* include data corresponding to patients having selected patient characteristics. For example, when an operating point is to be determined based on a binarized age of the patient, operating point dataset 524*c* may be created to include a configurable proportion of older patients and younger patients.

In some embodiments, operating point data set 524*c* is created to include ECGs associated with multiple pluralities of patient characteristics. For example, an operating point data set may be created for each of younger females, older females, younger males, and older males. In some embodiments, each operating point data set is created to have approximately the same prevalence of low EF samples.

In some embodiments, one operating point is used across patients of all patient characteristics. Accordingly, operating point dataset 524*c* may include ECG-TTE pairs for patients having any combination of patient characteristics.

In some embodiments, several operating points may be used, corresponding to several separate combinations of patient characteristics. In some such embodiments, operating point dataset 524*c* may include ECG-TTE pairs for patients having the several separate combinations of patient characteristics.

In various embodiments, one or more of training dataset 524*a*, tuning dataset 524*b*, or operating point dataset 524*c* may be created to omit noisy ECGs. In some embodiments, the noisy ECGs are omitted when a noise level exceeds a noise threshold. The noise threshold may be based on a high frequency component. For example, a prevalence of high-frequency data in ECG data above a noise threshold may indicate that the ECG data is noisy.

In some embodiments, noisy ECGs are included in one or more of datasets 524, and are excluded from one or more of datasets 524. For example, noisy ECGs may be included in training dataset 504*a*, and excluded from tuning data set 524*b* and operating point dataset 524*c*.

In various embodiments, training dataset 524*a*, tuning dataset 24*b*, and operating point dataset 524*c* contain various proportions of ECG-TTE pairs 520. In some embodiments, training dataset 524*a* includes 50% to 90% of the total ECG-TTE pairs 520, while the remaining ECG-TTE pairs 520 are split in configurable proportion between tuning dataset 524*b* and operating point dataset 524*c*.

Figure 6:
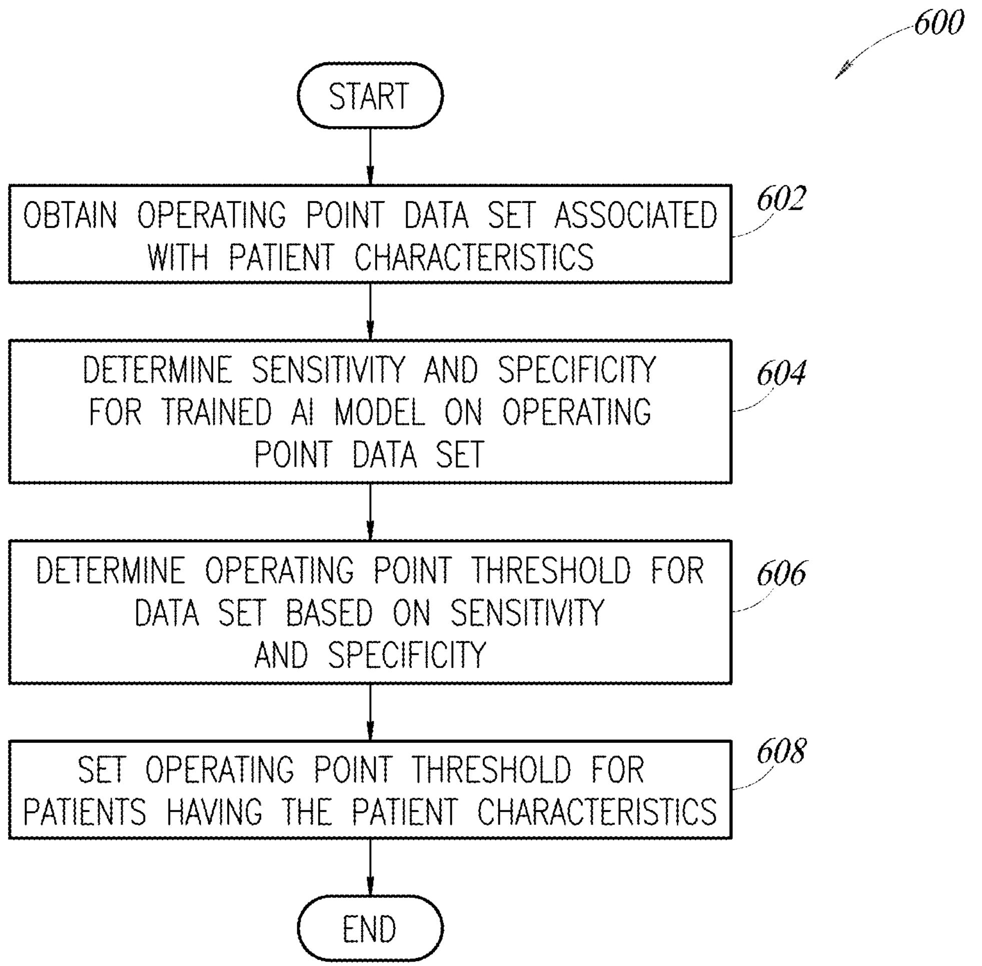
FIG. 6 is a logical flow diagram illustrating a process used to determine an operating point threshold for patients having certain characteristics according to some embodiments.
Figure 7:
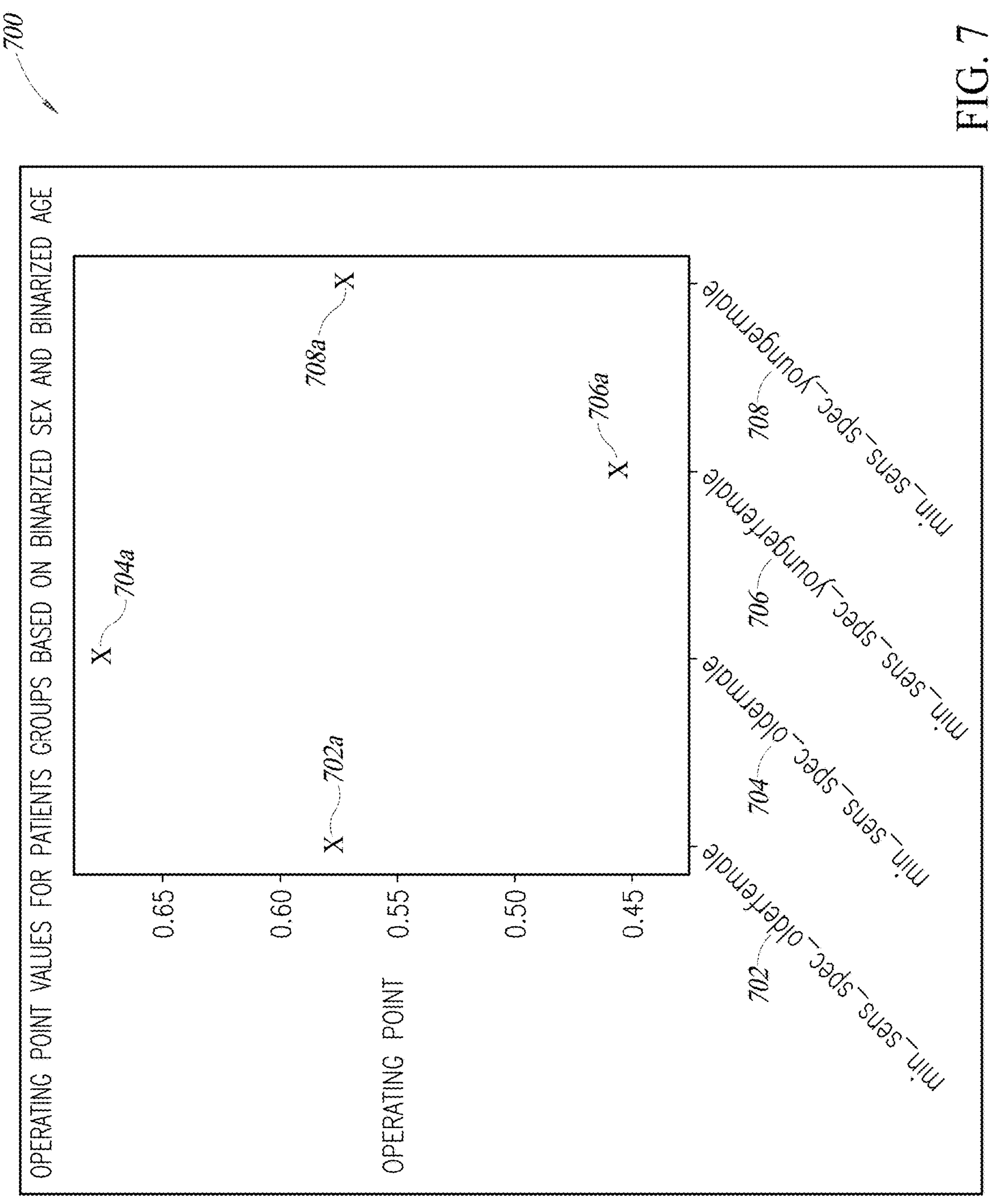
FIG. 7 is a scatter plot illustrating example operating points for patients having various characteristics according to some embodiments.

FIG. 6 is a logical flow diagram illustrating a process 600 used to determine an operating point threshold for patients having certain characteristics according to some embodiments. In classification problems, sensitivity refers to the true positive rate of a classifier, while specificity refers to the true negative rate of the classifier. For example, a classifier that classifies every patient as having low EF would have a sensitivity of 1 because every patient that has low EF is classified as having low EF. But such a classifier would also typically have poor specificity because all patients not having low EF are also classified as having low EF. Typically, a balance between sensitivity and specificity is preferable, such that the ensemble model is not substantially overinclusive or underinclusive in its predictions of low EF.

Sensitivity and specificity of the ensemble model may be adjusted by changing the operating point threshold. The operating point threshold is used to transform an overall score of low EF calculated by the ensemble model into a prediction of whether the patient has low EF. For example, a lower operating point threshold may lead to higher sensitivity and lower specificity because more patients are classified as having low EF, while a higher operating point threshold may lead to lower sensitivity and higher specificity. In various embodiments, block 210 of FIG. 2 employs embodiments of process 600 to obtain the operating point threshold for the patient based on patient characteristics.

Process 600 begins, after a start block, at block 602, where an operating point dataset associated with patient characteristics is obtained. In various embodiments, the operating point dataset is obtained to include data associated with patients having one or more patient characteristics. For example, when the operating point thresholds to be calculated are based on the binarized sex of patients, an operating point dataset corresponding to patients with female sex is obtained, and an operating point dataset corresponding to patients with male sex is obtained. In some embodiments, the operating point dataset includes a configurable proportion of each class of a binarized or otherwise quantized characteristic. For example, an operating point dataset associated with binarized sex may be include 50% male ECG-TTE pairs and 50% female ECG-TTE pairs.

In some embodiments, binarization of patient characteristics into two classes may be determined based on a threshold value. For example, age may be binarized into younger for patients younger than age 65 and older for patients 65 and older. In another example, BMI may be binarized into a group of low BMI and a group of high BMI, wherein BMIs above a $90^{th}$ percentile of BMIs are in the group of high BMIs, and wherein BMIs below the $90^{th}$ percentile are in the group of low BMIs.

In some embodiments, one or more patient characteristics are quantized into more than two discrete groups. For example, BMI may be quantized into four groups such as BMIs less than 18.5, BMIs between 18.5 and 25, BMIs between 25 and 30, and BMIs greater than 30. Similarly, institution may be quantized into several groups corresponding to each of the institutions that contributed ECG data to the dataset. After block 602, process 600 continues to block 604.

At block 604, a sensitivity and specificity for a trained AI model on the operating point dataset is determined. In some embodiments, the sensitivity and specificity comprise a receiver operating characteristic (ROC) graph. In some embodiments, the sensitivity and specificity comprise multiple pairs of corresponding sensitivity and specificity values. After block 604, process 600 continues to block 606.

At block 606, an operating point threshold is determined for the dataset based on the sensitivity and specificity. In some embodiments, the operating point threshold is determined to optimize a Youden's index computed using the sensitivity and specificity. In some embodiments, the operating point threshold is determined to optimize an absolute difference between the sensitivity and the specificity. In some embodiments, the operating point threshold is determined to optimize an F1 score calculated using the sensitivity and specificity. In some embodiments, the operating point threshold is determined to optimize an F2 score calculated using the sensitivity and specificity. In various embodiments, the operating threshold is determined to optimize any metric based on the sensitivity and the specificity. In various embodiments, the operating threshold is determined to optimize any other metric, such as positive predictive value (i.e. "PPV"), etc. After block 606, process 600 continues to block 608.

At block 608, an operating point threshold is set for patients having the patient characteristics. Accordingly, when an overall score of low EF is determined using ECG data associated with a patient having the patient characteristics, the operating point threshold is used to determine whether the overall score of low EF indicates that the patient has low EF. Examples of various operating point thresholds for patients having various patient characteristics are depicted in FIG. 7.

FIG. 7 is a scatter plot 700 illustrating operating points for patients having various characteristics according to some embodiments. As discussed herein, setting separate operating point thresholds for patients having various characteristics enables the ensemble model to perform adequately for patients having various characteristics. For example, when a same operating point is used for all patients, the ensemble model may perform differently across certain groups of patients, displaying significant variation of sensitivity and specificity. Selecting separate operating points for separate groups of patients enables the sensitivity and specificity to be tuned with respect to each group of patients. For example, it may be desirable for the ensemble model to satisfy certain standards of specificity and sensitivity, such as at least 80% sensitivity and at least 80% sensitivity, with respect to each relevant group of patients.

In the example shown in FIG. 7, patients are divided into four groups based on binarized age and binarized sex including older females 702, older males 704, younger females 706, and younger males 708.

Older females 704 have a corresponding threshold operating point 702*a*. Older males have a corresponding threshold operating point 704*a*. Younger females 706 have a corresponding threshold operating point 706*a*. Younger males 708 have a corresponding threshold operating point 708*a*.

While FIG. 7 illustrates threshold operating points for groups of patients defined by binarized sex and binarized age, the disclosure is not so limited. In various embodiments, threshold operating points may be determined for any subgroup of patients or any combination thereof. For example, an operating point threshold may be determined for a subgroup defined by age, sex, race, ethnicity, blend of race and ethnicity, hospital setting, body mass index (BMI), institution at which the ECG data was collected, history of conduction disorder, history of coronary re-vascularization, history of diabetes, history of myocardial infarction, ECG manufacturer, ECG model, etc., or any combination thereof. For example, threshold operating points may be calculated for each combination of binarized age, binarized sex, and binarized BMI. Furthermore, the groups of patients are not necessarily binarized. In various embodiments, a patient characteristic may be quantized into any number of classes or subgroups. For example, patient age may be quantized into groups corresponding to ages 0-50, 51-60, 61-70, 71-80, and over 80.

Figure 8:
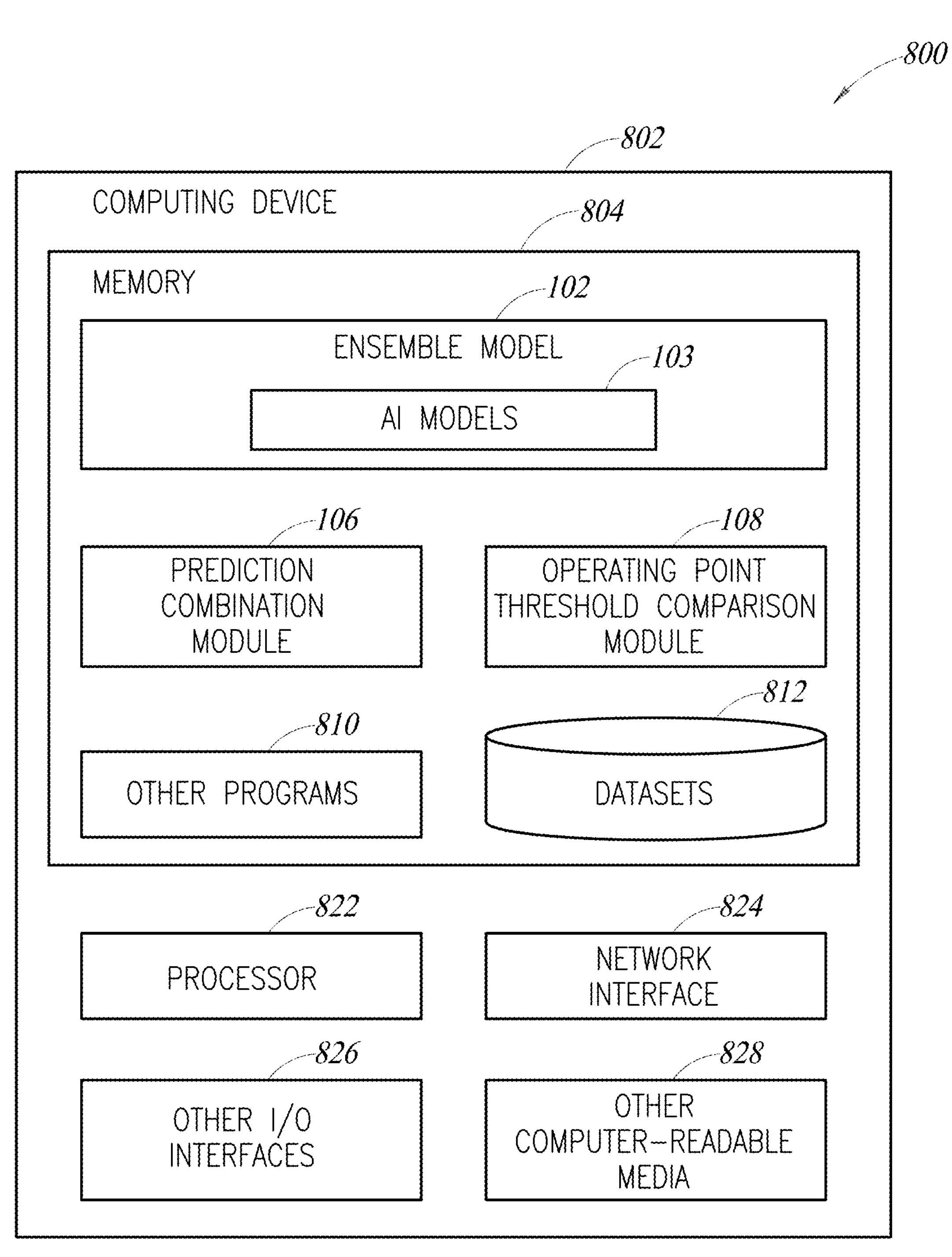
FIG. 8 is a block diagram illustrating elements of an example computing device used to implement embodiments described herein.

FIG. 8 is a block diagram illustrating elements of example computing system 800 used to implement embodiments described herein. System 800 includes computing device 802.

Computing device 802 includes memory 804, processor 822, network interfaces 824, other I/O interfaces 826, and other computer-readable media 828.

Processor 822 may include one or more central processing units, circuitry, or other computing components or units-collectively referred to as a processor or one or more processors—that are configured to performed embodiments herein or to execute computer instructions to perform embodiments described herein. In some embodiments, a single processor may operate individually to perform embodiments described herein. In other embodiments, a plurality of processors may operate to collectively perform embodiments described herein, such that one or more processors may operate to perform some, but not all, of the embodiments described herein.

Memory 804 may include one or more various types of non-volatile and/or volatile storage technologies. Examples of memory 804 may include, but are not limited to, flash memory, hard disk drives, optical drives, solid-state drives, various types of random access memory (RAM), various types of read-only memory (ROM), other computer-readable storage media (also referred to as processor-readable storage media), or the like, or any combination thereof. Memory 804 may be utilized to store information, including computer-readable instructions that are utilized by processor 822 to perform actions, including embodiments described herein.

Memory 804 may store ensemble model 102, prediction combination module 106, operating point threshold comparison module 108, other programs 810, and datasets 812.

Ensemble model 102 includes one or more AI models 103, wherein each AI model is trained to determine a score of low ejection fraction based on ECG data.

Prediction combination module 106 is configured to produce a combination of each score of low ejection fraction determined by the one or more AI models 103. In some embodiments, prediction combination module 106 produces an average of each score of low ejection fraction.

Operating point threshold comparison module 108 is configured to compare the combined score of low ejection fraction produced using prediction combination module 106 to an operating point threshold. In various embodiments, operating point threshold comparison module 108 selects an operating point threshold based on one or more characteristics of the patient for which low EF is to be predicted. In some embodiments, the one or more characteristics are provided as input to computing device 802. For example, the patient's binarized sex and age may be provided, indicating a corresponding operating point threshold to be used in predicting low EF for the patient. In some embodiments, more than one relevant operating point threshold may correspond to the one or more characteristics provided. For example, an operating point threshold based only on binarized sex, operating point threshold based only on binarized age, and an operating point threshold based on both binarized sex and binarized age may be available. In some such embodiments, the operating point threshold corresponding to the largest number of patient characteristics is selected.

Other programs 810 may include operating systems, applications, or other programs.

Datasets 812 may include training dataset 524*a*, tuning dataset 524*b*, or operating point dataset 524*c* of FIG. 5.

Network interfaces 824 is configured to communicate with other computing devices via a communication network that may include any combination of wired or wireless connections.

Other I/O interfaces 826 may include interfaces for various other input or output devices, such as audio interfaces, other video interfaces, USB interfaces, physical buttons, keyboards, haptic interfaces, tactile interfaces, or the like. Other computer-readable media 728 may include other types of stationary or removable computer-readable media, such as removable flash drives, external hard drives, etc.

Other computer-readable media 828 may include various computer-readable media stored on removable flash drives, external hard drives, etc.

The following is a summarization of the claims as filed.

A method may include: obtaining electrocardiogram (ECG) data for a patient; providing the ECG data as input to a plurality of trained artificial intelligence (AI) models, wherein each trained AI model is trained to determine a score of low ejection fraction (EF) based on the ECG data; determining, using each trained AI model, a score of low EF based on the ECG data; determining an overall score of low EF based on a combination of the scores of low EF determined by each of the trained AI models; obtaining an operating point threshold for the patient based on a plurality of patient characteristics; comparing the overall score of low EF to the operating point threshold; and determining an indication of low EF for the patient based on the comparison.

In some embodiments, obtaining the operating point threshold includes: obtaining the operating point threshold that minimizes a difference between a sensitivity and a specificity of indications of low EF determined using the plurality of trained AI models for patients having the plurality of patient characteristics.

In some embodiments, obtaining the operating point threshold for the patient includes: obtaining the operating point threshold for the patient based on the plurality of patient characteristics, wherein the plurality of patient characteristic includes a representation of sex of the patient.

In some embodiments, obtaining the operating point threshold for the patient includes: obtaining the operating point threshold for the patient based on the plurality of patient characteristics, wherein the plurality of patient characteristics includes a representation of age of the patient.

In some embodiments, obtaining the operating point threshold includes: obtaining the operating point threshold that minimizes a difference between a sensitivity and a specificity of indications of low EF determined using the plurality of trained AI models, wherein the operating point threshold is based on the plurality of patient characteristics that includes a representation of sex of the patient and a representation of age of the patient.

In some embodiments, each trained AI model has a same architecture, and each trained AI model was trained using a different initial seed for weight initialization.

In some embodiments, determining the overall score of low EF based on the combination of the scores of low EF includes: determining the overall score of low EF based on an average of the scores of low EF.

In some embodiments, each trained AI model in the plurality of trained AI models includes a convolutional neural network (CNN), wherein the CNN includes one or more convolutional blocks and one or more fully connected blocks.

In some embodiments, a trained AI model of the plurality of trained AI models is trained by: obtaining transthoracic echocardiogram (TTE) data for a patient; obtaining ECG data for the patient; generating training data by labelling the ECG data based on whether the TTE data indicates that the patient has low EF; and training the at least one trained AI model using the training data.

In some embodiments, obtaining the ECG data for the patient comprises: determining a TTE result date corresponding to a date of an earliest TTE result in the TTE data that indicates low EF; and obtaining the ECG data for the patient that is within a time window of the TTE result date.

In some embodiments, the method further includes: automatically scheduling the patient for a transthoracic echocardiogram based on the binary low EF prediction.

In some embodiments, the binary low EF prediction is made while the ECG data is being obtained from the patient.

In some embodiments, obtaining the ECG data for the patient includes: determining that an earliest TTE result in the TTE data indicates low EF; obtaining a TTE result date of the earliest TTE result; obtaining the ECG data for the patient that includes an ECG result having an ECG result date closest to the TTE result date among ECG results of the ECG data, wherein the ECG result date is within a time window of the TTE result date.

In some embodiments, generating the training data by labeling the ECG data based on whether the corresponding TTE data indicates low EF includes: generating the training data by labeling the ECG data based on whether an EF value of the corresponding TTE data is below a threshold EF value.

In some embodiments, obtaining the ECG data for the patient includes: obtaining non-paced ECG data for the patient.

In some embodiments, the training data includes a prevalence of low EF results between five percent and twenty percent.

In some embodiments, a system includes: one or more processors; and one or more non-transitory computer-readable memories storing instructions executable by the one or more processors to cause the system to: obtain electrocardiogram (ECG) data for a patient; provide the ECG data to an ensemble of trained artificial intelligence (AI) models, wherein each trained AI model of the ensemble is trained to determine a score of low ejection fraction (EF) based on the ECG data; determine a combined score of low EF for the patient based on a weighted combination of the scores of low EF determined by each trained AI model; obtain an operating point threshold for the patient based on a representation of age of the patient and a representation of sex of the patient; compare the combined score of low EF to the operating point threshold; and determine an indication of low EF for the patient based on the comparison.

In some embodiments, the one or more processors obtain the operating point threshold for the patient by being further configured to: obtain the operating point threshold that minimizes a difference between a sensitivity and a specificity of indications of low EF determined using the ensemble of trained AI models for other patients having the age of the patient and the sex of the patient.

In some embodiments, a non-transitory computer-readable medium storing instructions executable by one or more processors to cause actions to be performed, the actions including: obtaining electrocardiogram (ECG) data for a patient; providing the ECG data to an ensemble of trained artificial intelligence (AI) models, wherein each trained AI model of the ensemble is trained to determine a risk of low ejection fraction (EF) based on the ECG data; determining, using one or more fully connected layers, a combined risk of low EF for the patient based on the risks of low EF determined by each trained AI model; obtaining an operating point threshold for the patient based on a representation of age of the patient and a representation of sex of the patient; comparing the overall risk of low EF to the operating point threshold; and determining an indication of low EF prediction for the patient based on the comparison.

In some embodiments, obtaining the operating point threshold for the patient includes: obtaining the operating point threshold that minimizes a difference between a sensitivity and a specificity of indications of low EF determined using the ensemble of trained AI models for other patients having the sex of the patient and the age of the patient.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:

obtaining electrocardiogram (ECG) data for a subject, wherein obtaining the ECG data for the subject comprises obtaining non-paced ECG data for the subject;

providing the ECG data as input to a plurality of trained artificial intelligence (AI) models, wherein each trained AI model is trained to determine a score of low ejection fraction (EF) based on the ECG data;

determining, using each trained AI model, a score of low EF based on the ECG data;

determining an overall score of low EF based on a combination of the scores of low EF determined by each of the trained AI models;

selecting, from a plurality of operating point thresholds that correspond to combinations of subject characteristics, an operating point threshold for the subject based on a plurality of subject characteristics of the subject;

comparing the overall score of low EF to the operating point threshold; and determining an indication of low EF for the subject based on the comparison.

2. The method of claim 1, wherein selecting the operating point threshold comprises:

selecting the operating point threshold that minimizes a difference between a sensitivity and a specificity of indications of low EF determined using the plurality of trained AI models for subjects having the plurality of subject characteristics.

3. The method of claim 1, wherein selecting the operating point threshold for the subject comprises:

selecting the operating point threshold for the subject based on the plurality of subject characteristics, wherein the plurality of subject characteristics includes a representation of sex of the subject.

4. The method of claim 1, wherein selecting the operating point threshold for the subject comprises:

selecting the operating point threshold for the subject based on the plurality of subject characteristics, wherein the plurality of subject characteristics includes a representation of age of the subject.

5. The method of claim 1, wherein selecting the operating point threshold comprises:

selecting the operating point threshold that minimizes a difference between a sensitivity and a specificity of indications of low EF determined using the plurality of trained AI models, wherein the operating point threshold is based on the plurality of subject characteristics that includes a representation of sex of the subject and a representation of age of the subject.

6. The method of claim 1, wherein each trained AI model has a same architecture, and wherein each trained AI model was trained using a different initial seed for weight initialization.

7. The method of claim 1, wherein determining the overall score of low EF based on the combination of the scores of low EF comprises:

determining the overall score of low EF based on an average of the scores of low EF.

8. The method of claim 1, wherein each trained AI model in the plurality of trained AI models includes a convolutional neural network (CNN), wherein the CNN includes one or more convolutional blocks and one or more fully connected blocks.

9. The method of claim 1, wherein a trained AI model of the plurality of trained AI models is trained by:

obtaining transthoracic echocardiogram (TTE) data for a subject;

obtaining ECG data for the subject;

generating training data by labeling the ECG data based on whether the TTE data indicates that the subject has low EF; and training the trained AI model using the training data.

10. The method of claim 9, wherein obtaining the ECG data for the subject comprises:

determining a TTE result date corresponding to a date of an earliest TTE result in the TTE data that indicates low EF; and obtaining the ECG data for the subject that is within a time window of the TTE result date.

11. The method of claim 9, wherein obtaining the ECG data for the subject comprises:

determining that an earliest TTE result in the TTE data indicates low EF;

obtaining a TTE result date of the earliest TTE result; and obtaining the ECG data for the subject that includes an ECG result having an ECG result date closest to the TTE result date among ECG results of the ECG data, wherein the ECG result date is within a time window of the TTE result date.

12. The method of claim 9, wherein generating the training data by labeling the ECG data based on whether the corresponding TTE data indicates low EF comprises:

generating the training data by labeling the ECG data based on whether an EF value of the corresponding TTE data is below a threshold EF value.

13. The method of claim 9, wherein between five percent and twenty percent of samples in the training data are labeled as indicating low EF.

14. The method of claim 1, the method further comprising:

automatically scheduling the subject for a transthoracic echocardiogram based on the indication of low EF.

15. The method of claim 1, wherein the indication of low EF is determined while the ECG data is being obtained from the subject.

16. A system, comprising:

one or more processors; and one or more non-transitory computer-readable memories storing instructions executable by the one or more processors to cause the system to:

obtain electrocardiogram (ECG) data for a subject, wherein the ECG data for the subject comprises non-paced ECG data for the subject;

provide the ECG data to an ensemble of trained artificial intelligence (AI) models, wherein each trained AI model of the ensemble is trained to determine a score of low ejection fraction (EF) based on the ECG data;

determine a combined score of low EF for the subject based on a weighted combination of the scores of low EF determined by each trained AI model;

select, from a plurality of operating point thresholds that correspond to combinations of subject characteristics, an operating point threshold for the subject based on a representation of age of the subject and a representation of sex of the subject;

compare the combined score of low EF to the operating point threshold; and determine an indication of low EF for the subject based on the comparison.

17. The system of claim 16, wherein the one or more processors select the operating point threshold for the subject by being further configured to:

select the operating point threshold that minimizes a difference between a sensitivity and a specificity of indications of low EF determined using the ensemble of trained AI models for other subjects having the age of the subject and the sex of the subject.

18. A non-transitory computer-readable medium storing instructions executable by one or more processors to cause actions to be performed, the actions comprising:

obtaining electrocardiogram (ECG) data for a subject, wherein obtaining the ECG data for the subject comprises obtaining non-paced ECG data for the subject;

providing the ECG data to an ensemble of trained artificial intelligence (AI) models, wherein each trained AI model of the ensemble is trained to determine a risk of low ejection fraction (EF) based on the ECG data;

determining, using one or more fully connected layers, a combined risk of low EF for the subject based on the risks of low EF determined by each trained AI model;

selecting, from a plurality of operating point thresholds that correspond to combinations of subject characteristics, an operating point threshold for the subject based on a representation of age of the subject and a representation of sex of the subject;

comparing the combined risk of low EF to the operating point threshold; and determining an indication of low EF for the subject based on the comparison.

19. The non-transitory computer-readable medium of claim 18, wherein selecting the operating point threshold for the subject comprises:

selecting the operating point threshold that minimizes a difference between a sensitivity and a specificity of indications of low EF determined using the ensemble of trained AI models for other subjects having the sex of the subject and the age of the subject.

* * * * *